US012778992B2

(12) United States Patent
Weiss et al.

(10) Patent No.: US 12,778,992 B2
(45) Date of Patent: Nov. 3, 2026

(54) **COMPOSITION CONTAINING *BIFIDOBACTERIUM LACTIS* AND HUMAN MILK OLIGOSACCHARIDES AND APPLICATION THEREOF**

(71) Applicants: Inner Mongolia Yili Industrial Group Co., Ltd., Hohhot City (CN); INNER MONGOLIA DAIRY TECH RES INSTITUTE CO LTD, Hohhot City (CN)

(72) Inventors: Gisela Adrienne Weiss, Hohhot City (CN); Carolien Annika Van Loo-Bouwman, Hohhot City (CN); Gerrit Smit, Hohhot City (CN); Wendan Wang, Hohhot City (CN); Ignatius Man-Yau Szeto, Hohhot City (CN); Fangjie Gu, Hohhot City (CN); Biao Liu, Hohhot City (CN)

(73) Assignees: Inner Mongolia Yili Industrial Group Co., Ltd., Hohhot City (CN); Inner Mongolia Dairy Tech Res Institute Co Ltd, Hohhot City (CN)

( * ) Notice: Subject to any disclaimer, the term of this patent is extended or adjusted under 35 U.S.C. 154(b) by 515 days.

(21) Appl. No.: 18/253,171

(22) PCT Filed: Nov. 16, 2021

(86) PCT No.: PCT/CN2021/130978
§ 371 (c)(1),
(2) Date: May 16, 2023

(87) PCT Pub. No.: WO2022/100758
PCT Pub. Date: May 19, 2022

(65) Prior Publication Data
US 2024/0000868 A1 Jan. 4, 2024

(30) Foreign Application Priority Data
Nov. 16, 2020 (CN) ........................ 202011279614.X

(51) Int. Cl.
*A61K 35/745* (2015.01)
*A23L 33/00* (2016.01)
*A61K 31/702* (2006.01)
*A61K 35/00* (2006.01)
*A61P 31/04* (2006.01)
*A61P 37/04* (2006.01)

(52) U.S. Cl.
CPC .......... *A61K 35/745* (2013.01); *A61K 31/702* (2013.01); *A61P 31/04* (2018.01); *A61P 37/04* (2018.01); *A23L 33/40* (2016.08); *A23V 2400/531* (2023.08); *A61K 2035/115* (2013.01)

(58) Field of Classification Search
None
See application file for complete search history.

(56) References Cited

U.S. PATENT DOCUMENTS

| | | | |
|---|---|---|---|
| 12,022,844 | B2 | 7/2024 | Takahashi et al. |
| 2010/0260720 | A1 | 10/2010 | Sprenger |
| 2012/0171165 | A1 | 7/2012 | Buck et al. |
| 2012/0294840 | A1 | 11/2012 | Newburg et al. |
| 2018/0368460 | A1 | 12/2018 | Mcconnell et al. |
| 2019/0166897 | A1 | 6/2019 | Berger et al. |
| 2019/0224254 | A1 | 7/2019 | Kyle et al. |
| 2021/0068414 | A1 | 3/2021 | Takahashi et al. |

FOREIGN PATENT DOCUMENTS

| | | | |
|---|---|---|---|
| CN | 101909644 | A | 12/2010 |
| CN | 102511714 | A | 6/2012 |
| CN | 204587639 | U | 8/2015 |
| CN | 103589658 | A | 1/2016 |
| CN | 108541221 | A | 9/2018 |
| CN | 108741083 | A | 11/2018 |
| CN | 109561723 | A | 4/2019 |
| CN | 110506793 | A | 11/2019 |
| CN | 110839702 | A | 2/2020 |
| CN | 110846241 | A | 2/2020 |
| CN | 110959867 | A | 4/2020 |
| CN | 111935995 | A | 11/2020 |
| EP | 2072052 | A1 | 6/2009 |
| EP | 3335576 | A1 | 6/2018 |
| WO | 2004032639 | A1 | 4/2004 |
| WO | 2009077352 | A1 | 6/2009 |
| WO | 2012092160 | A1 | 7/2012 |
| WO | 2012158517 | A1 | 11/2012 |
| WO | 2017021476 | A1 | 2/2017 |

(Continued)

OTHER PUBLICATIONS

International Search Report for Int'l Application No. PCT/CN2021/130978, Composition Containing Bifidobacterium Lactis and Human Milk Oligosaccharides and Application Thereof, Dated: Feb. 11, 2022, 11 pages (With English Translation).
Chinese Search Report for Chinese Application No. 202111357369.4, Composition Containing Bifidobacterium Lactis and Human Milk Oligosaccharides and Application Thereof, Dated: Nov. 14, 2022, 5 pages (With English Translation).
Written Opinion for Int'l Application No. PCT/CN2021/130978, "Composition Containing Bifidobacterium Lactis and Human Milk Oligosaccharides and Application Thereof", Dated: Feb. 11, 2022, 7 pages (With English Translation).
Arunachalam K et al., Enhancement of natural immune function by dietary consumption of Bifidobacterium lactis (HN019), European Journal of Clinical Nutriton, vol. 54 No. 3, Mar. 1, 2000.
Ackerman Dorothy L. et al, Antimicrobial and Antibiofilm Activity of Human Milk Oligosaccharides against *Streptococcus agalactiae, Staphylococcus aureus,* and Acinetobacter baumannii, ACS Infectious Diseases, vol. 4, No. 3, Mar. 9, 2018.

(Continued)

*Primary Examiner* — Brian Gangle
(74) *Attorney, Agent, or Firm* — Hamilton, Brook, Smith & Reynolds, P.C.

(57) ABSTRACT

The present disclosure provides a composition comprising *Bifidobacterium lactis* and human milk oligosaccharides (HMOs) and use thereof. The composition is capable of effectively enhancing resistance of an organism to *Staphylococcus aureus* infection, improving innate immunity of an organism, and/or anti-aging, and can be added to various health foods and healthcare foods.

14 Claims, 5 Drawing Sheets

(56) References Cited

FOREIGN PATENT DOCUMENTS

| | | | |
|---|---|---|---|
| WO | 2017103850 | A1 | 6/2017 |
| WO | 2018024440 | A1 | 2/2018 |

OTHER PUBLICATIONS

Supplementary European Search Report for EP Application No. 21891278 "Composition Containing Bifidobacterium Lactis and Human Milk Oligosaccharides and Application Thereof" , dated Sep. 27, 2024.

International Preliminary Report on Patentability for Int'l Application No. PCT/CN2021/130978, "Composition Containing Bifidobacterium Lactis and Human Milk Oligosaccharides and Application Thereof", Dated: May 16, 2023 (With English Translation).

Written Opinion and Search Report for Singapore patent application No. 11202304925V issued on Apr. 30, 2026.

gentamicin

*Bifidobacterium lactis*
HN019

COMPOSITION CONTAINING *BIFIDOBACTERIUM LACTIS* AND HUMAN MILK OLIGOSACCHARIDES AND APPLICATION THEREOF

This application is the U.S. National Stage of International Application No. PCT/CN2021/130978, filed Nov. 16, 2021, which designates the U.S., published in Chinese, and claims priority under 35 U.S.C. § 119 or 365(c) to Chinese Application No. 202011279614.X, filed Nov. 16, 2020. The entire teachings of the above applications are incorporated herein by reference.

TECHNICAL FIELD

The present disclosure mainly relates to a probiotic-prebiotic composition for enhancing resistance of an organism to *Staphylococcus aureus* infection and the use thereof, more particularly to a composition comprising *Bifidobacterium lactis* HN019 and human milk oligosaccharides (HMOs), which can effectively enhance resistance of an organism to *Staphylococcus aureus* infection, and can be added to various health foods and healthcare foods.

BACKGROUND

Over the last millennium, it has been documented in the medical literature that infants who were not breastfed suffered higher morbidity and mortality. Breast milk not only provides necessary nutrition for infants, but contains active ingredients that provide support for the development of infants' intestinal tract and immunity. Compared with formula-fed infants, breastfed infants have a higher relative abundance of beneficial bacteria in their intestinal flora, especially Bifidobacteria and lactic acid bacteria.

Breast milk establishes healthy intestinal flora for newborns by delivery of microbiota and active ingredients such as HMOs and cytokines in breast milk. An infant takes up $10^7$ to $10^8$ bacteria every day through breast milk, including lactic acid bacteria and Bifidobacteria. These bacteria are transferred directly to the infant through breast milk, and some of them can colonize the infant's intestinal tract, promoting establishment of intestinal flora in the early stage of life. The establishment of intestinal flora in an infant has both short-term and life-long effects on the development of the intestinal tract as well as on the immune system and the health.

Human milk oligosaccharides (HMOs) are the third most abundant substance in human milk after lactose and fat. The total content thereof varies according to different stages of lactation, and is approximately 12 to 14 g/L in mature milk, and approximately 20 to 24 g/L in colostrum. In the structure of each human milk oligosaccharide, a lactose is present at the reducing end, and most HMOs have a polylactosamine skeleton, with fucose and/or sialic acid at the end of the chain. Human milk oligosaccharides are mainly composed of three types: (1) fucosyl-based oligosaccharides, represented by 2'-fucosyl oligosaccharide and 3'-fucosyl oligosaccharide; (2) sialyl-based oligosaccharides, represented by 3'-sialyllactose and 6'-sialyllactose; (3) oligosaccharides formed by a core sugar chain structure without a fucosyl or sialyl group, represented by lacto-N-tetraose and lacto-N-neotetraose.

The presence and content of HMOs vary among individuals and are associated with the Lewis secretor phenotype of the mother. Since the raw material of infant formula powder is generally cow's milk which usually contains little or no such oligosaccharides, HMOs are a gap that must be bridged to make an infant formula closer to human milk.

In the 1990s, 2'-fucosyllactose (2'-FL), an HMO present in most breast milk, was found to be effective in attenuating the toxicity of stable toxins in *Escherichia. coli*. In 2003, this oligosaccharide was reported to inhibit the attachment and infection by *Campylobacter jejuni*. Subsequently, the three major functions of HMOs were gradually discovered and reported: (1) inhibiting attachment and infection by certain pathogenic bacteria; (2) serving as a prebiotic to promote the growth of bacteria in the intestinal symbiotic system; and (3) directly retarding the inflammatory response of mucous membranes to noxious stimuli. The first trial with 2'-FL as a clinical intervention demonstrated that its addition in a low-calorie formula was not only safe but also allowed formula-fed infants to grow at a rate comparable to that of breastfed infants. 2'-FL has also been used as a nutritional supplement for adults to relieve irritable bowel syndrome or inflammatory bowel diseases, or as a prebiotic to maintain the balance of intestinal flora.

Intestinal flora is an important component of the human intestinal micro-ecosystem and plays an important role in human health. For example, it provides essential nutrients, produces vitamin K, assists the digestive process, and promotes angiogenesis and intestinal nerve functioning. Both prebiotics and probiotics are regarded as microecological management tools to improve the health of an organism, and can modify, regulate, and reorganize the existing intestinal flora.

At present, in the fields of infant formula powder, supplementary food and nutritional supplements, there is a need for a solution to relieve an intestinal discomfort of infants and enhance their ability to resist infection by pathogenic bacteria such as *Staphylococcus aureus*. Furthermore, for children over 3 years old, adolescents and adults, there is also a need for a solution to relieve an intestinal discomfort and enhance their ability to resist infection by pathogenic bacteria such as *Staphylococcus aureus*.

As a model organism, *Caenorhabditis elegans* (*C. elegans*) has a great prospect of application in preclinical research and evaluation. It has a short life cycle (21 days), is highly replicable and reproducible, easy to operate, transparent, and easy to culture. Its genome has been fully sequenced, and a quarter of its genes are homologous to those in the human genome. Genetically mutated *C. elegans* generated by gene editing may serve as an experimental means for genetic analysis. Currently, *C. elegans* is not considered as an animal in European legislation. It is widely used in in vitro assays, for example in transcriptomics, proteomics, metabolomics and the like. As a model organism, it is often used as the first step in evaluation of a raw material. Prior to design of functional raw materials, in vitro enzymatic or cell assays, mouse modeling and clinical trials, *C. elegans* is often used as a high-throughput means to screen test raw materials for certain characteristics.

*Staphylococcus aureus* (*S. aureus*) is a Gram-positive bacterium belonging to the genus *Staphylococcus* and is a common food-borne pathogenic microorganism. It widely exists in the natural environment, and under certain conditions can produce enterotoxins and cause food poisoning. It has caused numerous incidents of food poisoning due to food-borne microbes. Upon infection by *Staphylococcus aureus*, people may have common food poisoning symptoms such as nausea, vomiting, and dizziness, and may even have symptoms such as enteritis, pneumonia, skin infection, wound infection and ulceration, meningitis, and the like.

SUMMARY OF THE INVENTION

An objective of the present disclosure is to provide a composition for enhancing resistance of an organism to *Staphylococcus aureus* infection.

The inventors have discovered in research that a combination of *Bifidobacterium lactis* and HMOs has a synergistic effect in enhancing resistance of an organism to *Staphylococcus aureus* infection.

Accordingly, in one aspect, the present disclosure provides a composition comprising *Bifidobacterium lactis* and human milk oligosaccharides (HMOs).

According to embodiments of the present disclosure, in the composition of the present disclosure, the *Bifidobacterium lactis* includes the bacterial strain *Bifidobacterium lactis* HN019.

The *Bifidobacterium lactis* HN019 strain is a commercial strain available from DuPont Danisco Co.

According to an embodiment of the present disclosure, in the composition of the present disclosure, the HMOs include one or more of 2'-fucosyllactose, 3'-fucosyllactose, lactose-N-tetraose, 3'-sialyllactose, and 6'-sialyllactose.

2'-fucosyllactose (2'-FL) is a trisaccharide structure formed by fucose and lactose, and is a representative of fucosyl-based oligosaccharides. Its commercial products are generally prepared by microbial fermentation and have the same structure as the oligosaccharide found in human milk.

3-fucosyllactose (3-FL) is a trisaccharide structure formed by fucose and lactose, a mutual isomer of 2'-fucosyllactose, and is a representative of fucosyl-based oligosaccharides. It is prepared by microbial fermentation and has the same structure as the oligosaccharide found in human milk.

Lacto-N-tetraose (LNT) is a hexasaccharide structure formed by lactose and a tetraose. It is prepared by microbial fermentation and is a representative of oligosaccharides having a core sugar chain as a basic structure and having no fucosyl or sialyl, and also has the same structure as the oligosaccharide found in human milk.

3'-sialyllactose (3'-SL) is a trisaccharide structure formed by sialic acid and lactose, a mutual isomer of 6'-sialyllactose, and is a representative of sialyl-based oligosaccharides. It is prepared by microbial fermentation and has the same structure as the oligosaccharide found in human milk.

6'-sialyllactose (6'-SL) is a trisaccharide structure formed by sialic acid and lactose, a mutual isomer of 3'-sialyllactose, and is a representative of sialyl-based oligosaccharides. It is prepared by microbial fermentation and has the same structure as the oligosaccharide found in human milk.

According to embodiments of the present disclosure, in the composition of the present disclosure, the content of 2'-fucosyllactose in the HMOs is 0 to 73%, preferably to 63%, further preferably 0 to 58%, even further preferably 2 to 55%, for example, 3 to 8%, 25 to 35%, or 51 to 56%, and more particularly 5%, 30%, or 53%. In the present disclosure, unless specifically indicated, the content of each HMO is based on a total weight of 100% of the sum of 2'-fucosyllactose, 3'-fucosyllactose, lacto-N-tetraose, 3'-sialyllactose, and 6'-sialyllactose.

According to embodiments of the present disclosure, in the composition of the present disclosure, the content of 3'-fucosyllactose in the HMOs is 0 to 61%, preferably 11 to 51%, further preferably 16 to 46%, even further preferably 20 to 44%, for example, 18 to 23%, 25 to 35%, or 40 to 45%, and more particularly 21%, 30%, or 41%.

According to embodiments of the present disclosure, in the composition of the present disclosure, the content of lacto-N-tetraose in the HMOs is 0 to 52%, preferably 6 to 42%, further preferably 11 to 37%, even further preferably 13 to 35%, for example, 13 to 18%, 22 to 27%, or 30 to 35%, and more particularly 16%, 25%, or 32%.

According to embodiments of the present disclosure, in the composition of the present disclosure, the content of 3'-sialyllactose in the HMOs is 0 to 42%, preferably 0 to 32%, further preferably 0 to 27%, even further preferably 2 to 25%, for example, 2 to 7%, 10 to 15%, or 20 to 25%, and more particularly 5%, 12%, or 22%.

According to embodiments of the present disclosure, in the composition of the present disclosure, the content of 6'-sialyllactose in the HMOs is 0 to 25%, preferably 0 to 15%, further preferably 0 to 10%, even further preferably 0 to 8%, for example, 3 to 8%, and more particularly 3% or 5%.

According to embodiments of the present disclosure, in the composition of the present disclosure, the HMOs are a combination of at least two, at least three, or at least four of 2'-fucosyllactose (2'-FL), 3-fucosyllactose (3-FL), lactose-N-tetraose (LNT), 3'-sialyllactose (3'-SL), and 6'-sialyllactose (6'-SL).

According to embodiments of the present disclosure, in the composition of the present disclosure, the HMOs include at least three or four of 2'-fucosyllactose, 3'-fucosyllactose, lactose-N-tetraose, 3'-sialyllactose, and 6'-sialyllactose in a weight ratio of (0 to 73%):(0 to 61%):(0 to 52%):(0 to 42%):(0 to 25%).

According to embodiments of the present disclosure, in the composition of the present disclosure, the HMOs include at least three or four of 2'-fucosyllactose, 3'-fucosyllactose, lactose-N-tetraose, 3'-sialyllactose, and 6'-sialyllactose in a weight ratio of (0 to 63%):(11 to 51%):(6 to 42%):(0 to 32%):(0 to 15%).

According to embodiments of the present disclosure, in the composition of the present disclosure, the HMOs include at least three or four of 2'-fucosyllactose, 3'-fucosyllactose, lactose-N-tetraose, 3'-sialyllactose, and 6'-sialyllactose in a weight ratio of (0 to 58%):(16 to 46%):(11 to 37%):(0 to 27%):(0 to 10%).

According to embodiments of the present disclosure, in the composition of the present disclosure, the HMOs include 2'-fucosyllactose, 3'-fucosyllactose, lactose-N-tetraose, 3'-sialyllactose, and 6'-sialyllactose in a weight ratio of (0 to 55%):(20 to 44%):(13 to 35%):(2 to 25%):(0 to 8%).

According to embodiments of the present disclosure, in the composition of the present disclosure, the HMOs include 2'-fucosyllactose, 3'-fucosyllactose, lactose-N-tetraose, 3'-sialyllactose, and 6'-sialyllactose in a weight ratio of (0 to 53%):(21 to 41%):(16 to 32%):(5 to 22%):(0 to 5%), preferably (5 to 53%):(21 to 41%):(16 to 32%):(5 to 22%):(0 to 5%), and more preferably (5 to 53%):(21 to 41%):(16 to 32%):(5 to 22%):(3 to 5%).

According to embodiments of the present disclosure, in the composition of the present disclosure, the HMOs include 2'-fucosyllactose, 3'-fucosyllactose, lactose-N-tetraose, 3'-sialyllactose, and 6'-sialyllactose in a weight ratio of (30 to 53%):(21 to 30%):(16 to 25%):(5 to 12%):(3 to 5%).

According to embodiments of the present disclosure, in the composition of the present disclosure, the HMOs include 2'-fucosyllactose, 3'-fucosyllactose, lactose-N-tetraose, 3'-sialyllactose, and 6'-sialyllactose in a weight ratio of (33 to 73%):(1 to 41%):(0 to 36%):(0 to 25%):(0 to 25%), preferably (43 to 63%):(11 to 31%):(6 to 26%):(0 to 15%):(0 to 15%), more preferably (48 to 58%):(16 to 26%):(11 to 21%):(0 to 10%):(0 to 10%), and most preferably (51 to 56%):(18 to 23%):(13 to 18%):(2 to 7%):(3 to 8%).

According to an embodiment of the present disclosure, in the composition of the present disclosure, the ratio of the *Bifidobacterium lactis* to the HMOs is ($1\times10^3$ to $1\times10^{12}$ CFU):(0.1 to 10 g), preferably ($1\times10^6$ to $1\times10^{10}$ CFU):(1 to 10 g). According to certain embodiments of the present disclosure, the ratio of the *Bifidobacterium lactis* to the HMOs is $1\times10^8$ CFU:0.08 to 0.3 g. The ratio of the *Bifidobacterium lactis* to the HMOs is based on their amounts in the same composition.

In a further aspect, the present disclosure provides the use of the composition in the manufacture of a food product or medicament for effectively enhancing resistance of an organism to *Staphylococcus aureus* infection, improving innate immunity of an organism, and/or anti-aging.

According to an embodiment of the present disclosure, in the use of the composition of the present disclosure, the organism includes an animal and human.

According to an embodiment of the present disclosure, in the use of the composition of the present disclosure, the enhancing resistance of an organism to *Staphylococcus aureus* infection includes: enhancing an individual's ability to prevent *S. aureus* infection, reducing the ability of *S. aureus* to infect an individual, and/or alleviating symptoms caused by *S. aureus* infection such as food poisoning (including nausea, vomiting and dizziness), enteritis, pneumonia, skin infection, wound ulceration, or meningitis.

According to an embodiment of the present disclosure, the composition of the present disclosure may be used to prepare various health foods, healthcare foods, and medicaments. Particularly, the food may be a liquid beverage, a solid beverage, an oral liquid, a diary product, a tablet, or a capsule. For example, it may be used as a supplement in infant food (including infant formula powder, supplementary food, nutritional supplement) and nutritional supplement or food for children at the age of 3 or above, adolescents and adults (e.g., milk powder), which may find broad applications. The medicament may be an oral preparation, or may be an external formulation, such as an ointment for application.

In another aspect, the present disclosure provides a method for enhancing resistance of an organism to *Staphylococcus aureus* infection, improving innate immunity of an organism, and/or anti-aging, which comprises: administering to the organism an effective amount of the composition according to the present disclosure. Here, the enhancing resistance of an organism to *Staphylococcus aureus* infection includes: enhancing an individual's ability to prevent *S. aureus* infection, reducing the ability of *S. aureus* to infect an individual, and/or alleviating food poisoning, enteritis, pneumonia, skin infection, wound ulceration, and/or meningitis caused by *S. aureus* infection in an individual. In certain embodiments of the present disclosure, the composition is administered to the organism in the form of food, wherein the food is a liquid beverage, a solid beverage, an oral liquid, a diary product, a tablet, or a capsule, such as milk powder, particularly infant formula powder. Preferably, *Bifidobacterium lactis* in the food is used in an amount of $1\times10^3$ to $1\times10^{12}$ CFU/day, and more preferably $1\times10^6$ to $1\times10^{11}$ CFU/day. Preferably, the HMOs in the food are used in an amount of to 15 g/day, further preferably 0.1 to 12 g/day, and more preferably 1.5 to 10 g/day.

The present disclosure further provides a food product comprising the composition according to the present disclosure.

According to an embodiment of the present disclosure, the *Bifidobacterium lactis* in the food product is used in an amount of $1\times10^3$ to $1\times10^{12}$ CFU/day, and preferably $1\times10^6$ to $1\times10^{11}$ CFU/day. In certain embodiments of the present disclosure, the *Bifidobacterium lactis* in the food product is used in an amount of $1\times10^8$ CFU/day.

According to an embodiment of the present disclosure, the HMOs in the food product are used in an amount of 0.015 to 15 g/day, further preferably 0.1 to 12 g/day, and more preferably 1.5 to 10 g/day.

The food product or medicament according to the present disclosure comprising the composition can enhance resistance of an organism to *Staphylococcus aureus* infection by including the composition.

Figure 1:
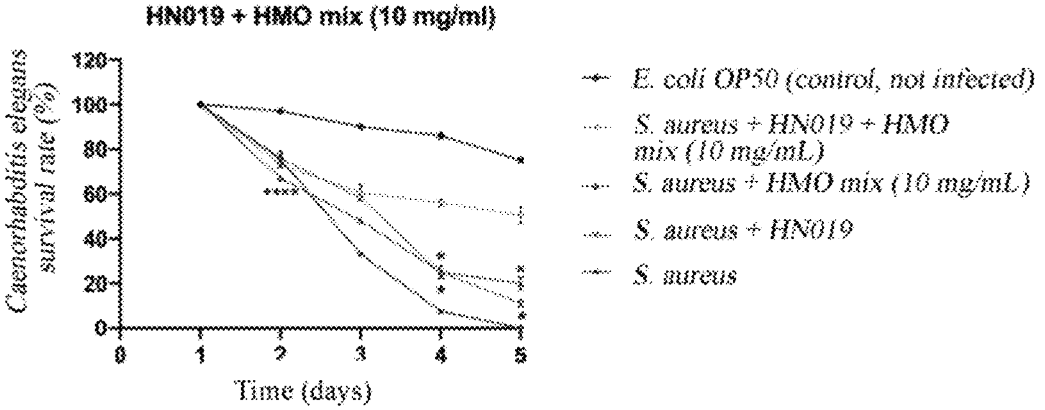
FIG. 1 shows the effect of a composition of 10 mg/mL of HMO mix A and *Bifidobacterium lactis* HN019 on the survival rate of *Caenorhabditis elegans* infected by *Staphylococcus aureus*. For each group indicated in the figure, the addition of intervening substance (probiotic and/or HMOs) in the infection stage is the same as that in the culture stage.

In the figures: * represents $p<0.05$,  represents $p<0.01$, * represents $p<0.001$, **** represents $p<0.0001$, NS represents no significant difference (not significant).

DETAILED DESCRIPTION OF THE INVENTION

In order to provide a better understanding of the technical features, purposes and advantageous effects of the present disclosure, the technical solutions of the present disclosure are described in details hereinafter, which should not be construed as limitation to the implementable scope of the present disclosure.

Example 1: Effects of a Composition of an HMO Mix and *Bifidobacterium lactis* HN019 on the Survival Rate of *Caenorhabditis elegans* Infected by *Staphylococcus aureus*

1. Experimental Materials and Methods 1.1 the Tested HMO Samples are Shown in Table 1.

TABLE 1

| Name | English abbreviation | Source |
|---|---|---|
| 2'-fucosyllactose | 2'-FL | Jennewein |
| 3-fucosyllactose | 3-FL | Jennewein |
| Lacto-N-Tetraose | LNT | Jennewein |
| 3'-sialyllactose | 3'-SL | Jennewein |
| 6'-sialyllactose | 6'-SL | Jennewein |
| HMO mix A of 5 HMOs | HMO mix | Jennewein |

In HMO mix A, the five HMOs were in a ratio of: 53% 2'-FL, 21% 3-FL, 16% LNT, 5% 3'-SL, and 5% 6'-SL.

A solution of HMOs was prepared with distilled water and incubated in dishes containing a nematode growth medium at different final concentrations (1, 10, 30 mg/mL, respectively).

The probiotic to be tested was grown in an MRS medium supplemented with 1% cysteine, and incubated overnight at 37° C. in an anaerobic environment. The cells were harvested and rinsed with physiological saline, the concentration of the bacteria was adjusted, and the bacteria were then inoculated on a plate containing a nematode growth medium at a final concentration of $1\times10^8$ CFU.

1.2 Nematode Infection Model

Nematodes of the same age were obtained and cultured in a dish containing a nematode agar medium (NGM medium, a nematode medium containing *E. coli* OP50 as food), and a composition of an HMO mix at varying dosages (8 mg/mL, 10 mg/mL, 30 mg/mL) and the probiotic ($1\times10^8$ CFU) was added for co-culturing (the total volume of liquid added to each nematode culture dish was 10 mL; for the test group having HMOs at a concentration of 10 mg/mL, the final amount of HMOs in each dish was 100 mg; for the test groups having HMOs at a concentration of 8 mg/mL and 30 mg/mL, the final amount of HMOs in each dish was 80 mg and 300 mg, respectively; thus, in each plate, the ratio of probiotic to HMOs was $1\times10^8$ CFU:80-300 mg). After the nematodes grew into an adult form, they were transferred to dishes inoculated with *Staphylococcus aureus* ATCC25923 at an amount of $10^8$-$10^9$ CFU/mL to simulate the infection by *Staphylococcus aureus*. For each group, the addition of the intervening substance (probiotic and/or HMOs) in the infection stage was the same as that in the culture stage. Two controls were set to respectively create the condition without pathogenic bacteria (nematode dishes containing *E. coli* OP50, i.e., the OP50 group), and the condition with pathogenic *S. aureus* infection but without any intervening material (dishes containing only *S. aureus*). Further groups wherein the intervening substance was added during the culture stage but not during the infection stage, and groups wherein the intervening substance was not added during the culturing stage but was added during the infection stage, were established.

After the nematodes were cultured for a few days, their survival rate was counted on a daily basis. If the nematodes did not respond to a platinum wire, they were considered dead. Two independent assays were carried out for each condition.

Statistical comparative analysis of the survival curves was carried out, and a log rank survival analysis of significance was carried out by using the GraphPad Prism 4 statistics software package. Differences in the effect on nematode survival between groups shown on each day were first analyzed by Two-way ANOVA, and then the comparison of the groups was done by a Tukey's post hoc test. Differences between the group of HMO mix alone or the probiotic alone and the group of the prebiotic-probiotic combination were marked with asterisks in the figures. One-way ANOVA and Dunnett's post hoc test were used to analyze the significant difference in the survival rates of each group on Day 3 or 5 after infection.

1.3 Disc Diffusion Test of Inhibition Zone

In order to determine whether the test substances per se had an antibacterial effect, a disc diffusion test of inhibition zone was carried out. Discs were prepared with sterile filter paper, the test substances HMO (10 mg/mL, 30 mg/mL) or probiotic ($1\times10^8$ CFU) were introduced thereto, and the discs were dried overnight under sterile conditions. *Staphylococcus aureus* ATCC25923 ($1.0\times10^6$ CFU/mL) was uniformly applied on the surface of an NGM agar plate, and then the discs were placed on the surface of the inoculated agar plate. Gentamicin (200 μg/mL) was used as a positive control. All plates were incubated at 37° C. for 18 hours. Presence or absence of a transparent ring formed around the discs was observed to determine whether the test substances were capable of directly inhibiting the growth of the bacterium or had antibacterial activity.

2. Experimental Results

Figure 2:
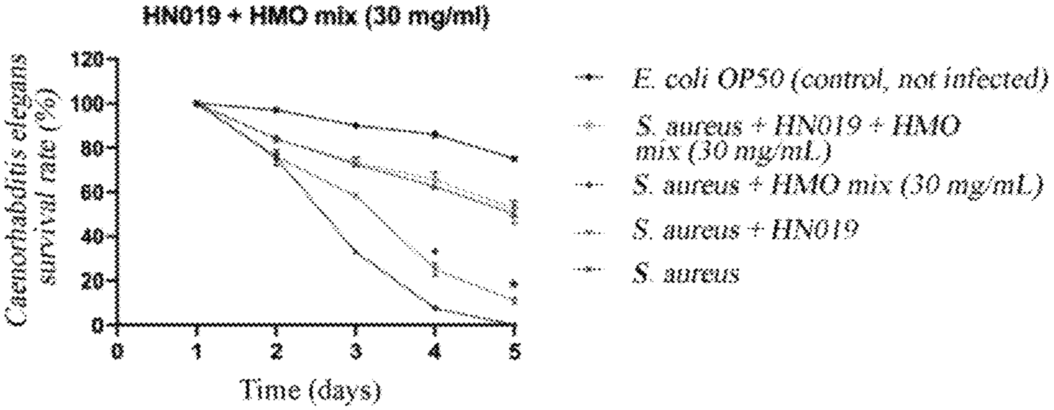
FIG. 2 shows the effect of a composition of 30 mg/mL of HMO mix A and *Bifidobacterium lactis* HN019 on the survival rate of *Caenorhabditis elegans* infected by *Staphylococcus aureus*. For each group indicated in the figure, the addition of intervening substance (probiotic and/or HMOs) in the infection stage is the same as that in the culture stage.

The effects of *Bifidobacterium lactis* HN019 and HMO mix A of five HMOs at two different doses on the survival rate of *C. elegans* infected by *Staphylococcus aureus* are shown in FIGS. 1 and 2. Throughout the entire experiment course, with the HMO mix at 10 mg/mL, the effect of the prebiotic-probiotic combination was significantly better than that of the HMO mix alone or the probiotic alone ($P<0.0001$). However, with the HMO mix A at 30 mg/mL, the combination of HMOs and probiotic did not show an advantage throughout the entire experiment course.

As shown in FIG. 1, with the HMO mix A at 10 mg/mL, the effects of the combination of the prebiotic HMOs and the probiotic HN019 on Days 4 and 5 were significantly better than those of the probiotic HN019 alone ($p<0.05$), and on Days 2, 4 and 5 were significantly better than those of the HMO mix alone (Day 2: $p<0.0001$; Days 4, 5: $p<0.05$). Regarding a synergistic effect, the survival rates with the combination of HMOs and probiotic were compared with those with the HMO mix alone or with the probiotic alone, and it was found that the survival rate with the combination of HMOs and probiotic was significantly higher than the sum of the survival rate with the HMO mix alone and the survival rate with the probiotic alone on both Days 4 and 5, indicating a synergistic effect of the combination of HMOs and probiotic (Table 2).

TABLE 2

| Days of experiment | *S. aureus* + HMO mix A (10 mg/mL) | *S. aureus* + HN019 | *S. aureus* + HN019 + HMO mix A (10 mg/mL) | Synergistic effect |
|---|---|---|---|---|
| 1 | 100 | 100 | 100 | No |
| 2 | 67 | 76 | 73 | No |
| 3 | 48 | 58 | 61 | No |
| 4 | 25 | 25 | 56 | Yes |
| 5 | 20 | 11 | 51 | Yes |

Figure 3:
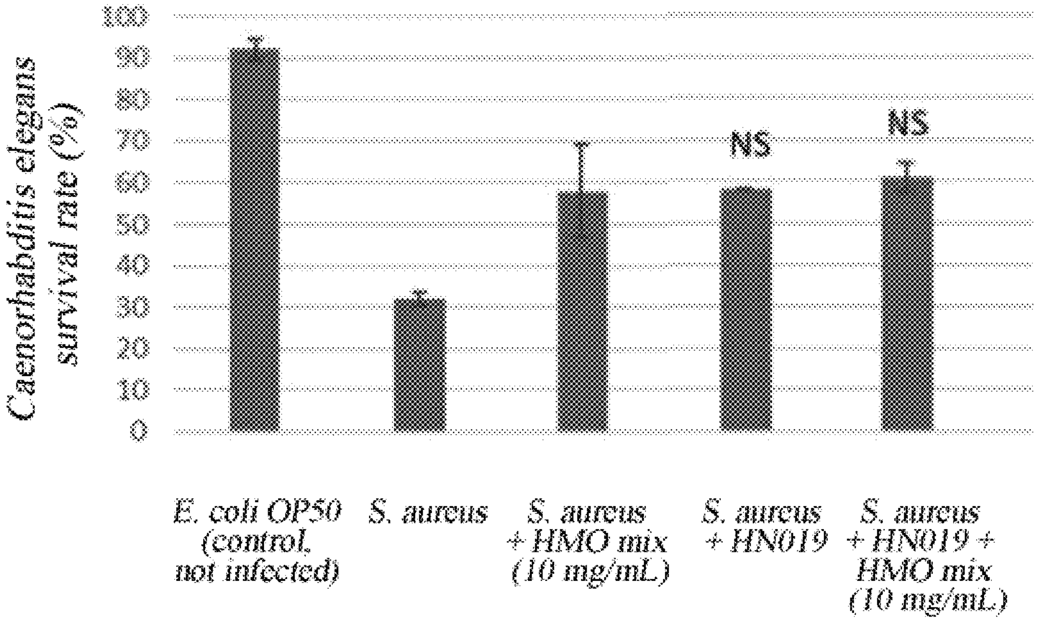
FIG. 3 shows the effect of a composition of HMO mix A and *Bifidobacterium lactis* HN019 on the survival rate of *Caenorhabditis elegans* on Day 3 after infection by *Staphylococcus aureus*. For each group indicated in the figure, the addition of intervening substance (probiotic and/or HMOs) in the infection stage is the same as that in the culture stage.
Figure 4:
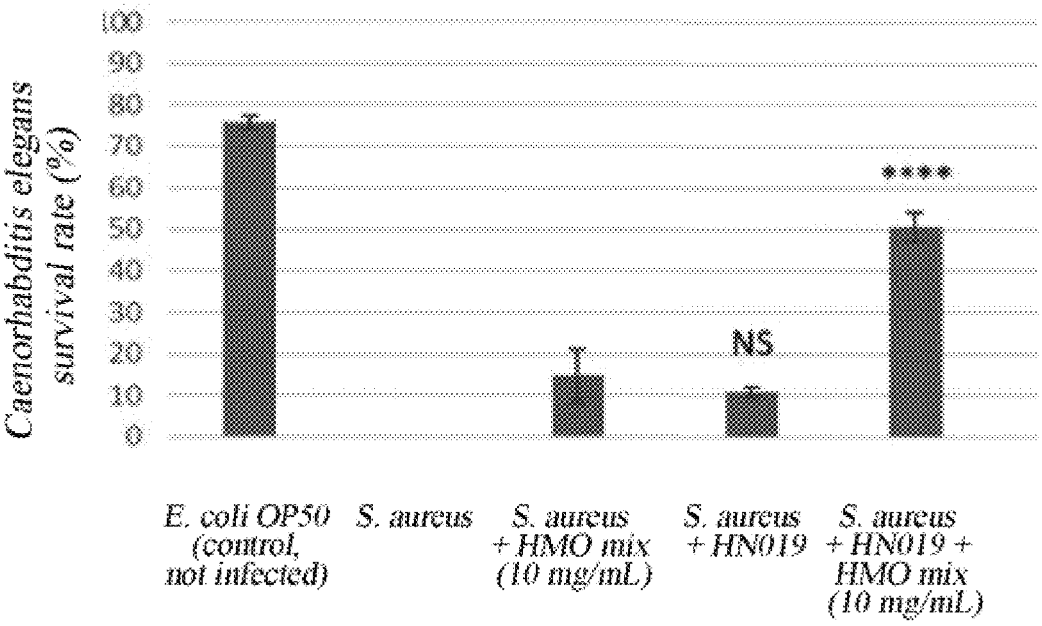
FIG. 4 shows the effect of a composition of HMO mix A and *Bifidobacterium lactis* HN019 on the survival rate of *Caenorhabditis elegans* on Day 5 after infection by *Staphylococcus aureus*. For each group indicated in the figure, the addition of intervening substance (probiotic and/or HMOs) in the infection stage is the same as that in the culture stage.

FIGS. 3 and 4 show a comparison of the effect of the combination of HMO mix A and the probiotic on the survival rate of *Caenorhabditis elegans* on Day 3 and Day 5 of infection. On Day 5 of infection, the combination of the prebiotic and the NH019 showed a better effect than the other test groups.

In addition, further experiments of the present disclosure demonstrate that the survival rate of *Caenorhabditis elegans* in the group with the intervention of the combination of the HMOs and HN019 in the culture stage but without any intervention in the infection stage was significantly higher than that of the groups without intervention either in the culture stage or in the infection stage.

Figure 5:
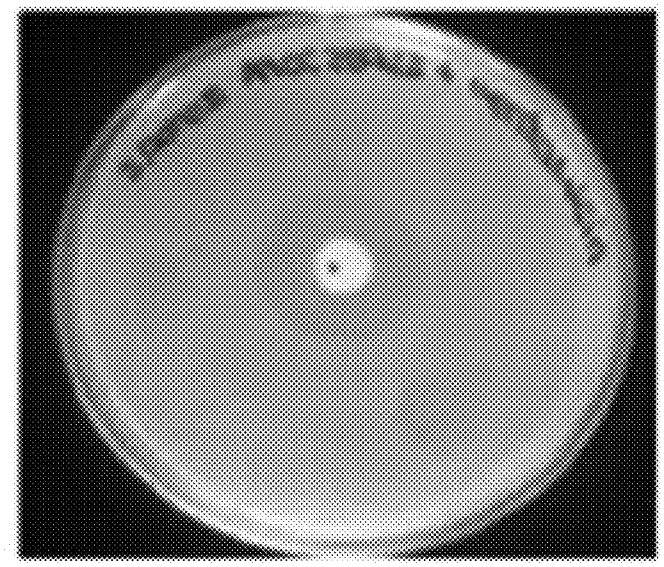
FIG. 5 is a picture of the results of the disc diffusion test of inhibition zone with gentamicin.
Figure 6:
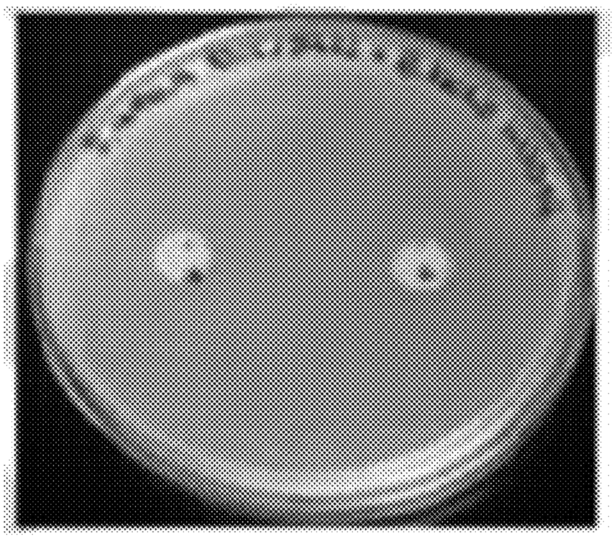
FIG. 6 is a picture of the results of the disc diffusion test of inhibition zone with *Bifidobacterium lactis* HN019.

In order to find out whether the protective effect of the combination of HMOs and probiotic against *Staphylococcus aureus* infection shown in the previous tests was due to a direct bactericidal or antibacterial effect, an inhibition zone test was carried out by culturing the test substances together with a bacterial population. As shown in FIGS. 5 and 6, the *Bifidobacterium lactis* HN019 strain did not form a transparent inhibition zone around the inoculation site (FIG. 6). The positive control gentamicin showed an antibacterial effect, as indicated by the formation of a transparent inhibition zone (FIG. 5). In addition, the inhibition zone test for each individual HMO at two different concentrations (10 mg/mL, 30 mg/mL) also showed a similar result, and none of the individual HMOs could directly inhibit the growth of *S. aureus*. Seen as such, the protective effect of the combination of HMOs and probiotic for *C. elegans* against *Staphylococcus aureus* infection shown in the present study was not due to a direct antibacterial action of the substances.

Example 2: Experiment of Efficacy in Improving Innate Immunity and Anti-Aging with a Combination of Different HMO Mixes and *Bifidobacterium lactis* HN019

In this example, the components and contents of the tested HMO mixes are shown in Table 3.

TABLE 3

| HMO mix | 2'-FL percentage | 3-FL percentage | LNT percentage | 3'-SL percentage | 6'-SL percentage |
|---|---|---|---|---|---|
| HMO mix A | 53 | 21 | 16 | 5 | 5 |
| HMO mix G | 5 | 41 | 32 | 22 | 0 |
| HMO mix H | 30 | 30 | 25 | 12 | 3 |

Experiment 1 for efficacy of the tested compositions (investigation of the preventive effect of the tested substances in terms of "enhancing resistance of an organism to *Staphylococcus aureus* infection, improving innate immunity of an organism, and/or anti-aging"): nematodes of the same age were taken and cultured in a dish containing a nematode agar medium, and a composition of HMO mix A (10 mg/mL) and the probiotic HN019 ($1\times10^8$ CFU) in a certain ratio was added for co-culturing until the nematodes grew into an adult form. Then the nematodes were transferred to an infection plate, and were infected by the pathogenic bacterium *Staphylococcus aureus* ATCC25923, without addition of the composition of HMOs and probiotic.

Experiment 2 for efficacy of the tested compositions (investigation of the therapeutic effect of the tested substances in terms of "enhancing resistance of an organism to *Staphylococcus aureus* infection, improving innate immunity of an organism, and/or anti-aging"): nematodes of the same age were taken and cultured in a dish containing a nematode agar medium. When the nematodes grew into an adult form, the nematodes were transferred to a plate supplemented with a composition of HMO mix A (10 mg/mL) and the probiotic HN019 ($1\times10^8$ CFU) in a certain ratio, and were infected by the pathogenic bacterium *Staphylococcus aureus* ATCC25923.

In addition, another group in which the composition of HMOs and probiotic was added in both the stages before and after the nematodes were infected was compared with the above two cases in Experiments 1 and 2 as a control group.

After the nematodes were cultured for a few days, their survival rate was counted on a daily basis. If the nematodes did not respond to a platinum wire, they were considered dead. Two control groups were further set, one without the pathogenic bacterium (a normal culturing plate supplemented with *E. coli* OP50 as food), and the other one as the infection control group (a plate with only *S. aureus* added). Two independent tests were performed for each condition. Statistical comparative analysis of the survival curves was carried out, and a log rank survival analysis of significance was carried out by using the GraphPad Prism 4 statistics software package.

Other operations during the experiments were done according to Example 1.

Experimental Results

1. Effect of Test Substances Co-Cultured with Nematodes Before and/or During Infection As mentioned above, in order to determine whether the test substances have a preventive effect, nematodes were co-cultured with HMO mix A and HN019 only before *S. aureus* infection. In order to determine whether the test substances have a therapeutic effect, nematodes were co-cultured with HMO mix A and HN019 only during *S. aureus* infection. Also included was a case where the test substances were co-cultured with the nematodes both before and during the infection.

Figure 7:
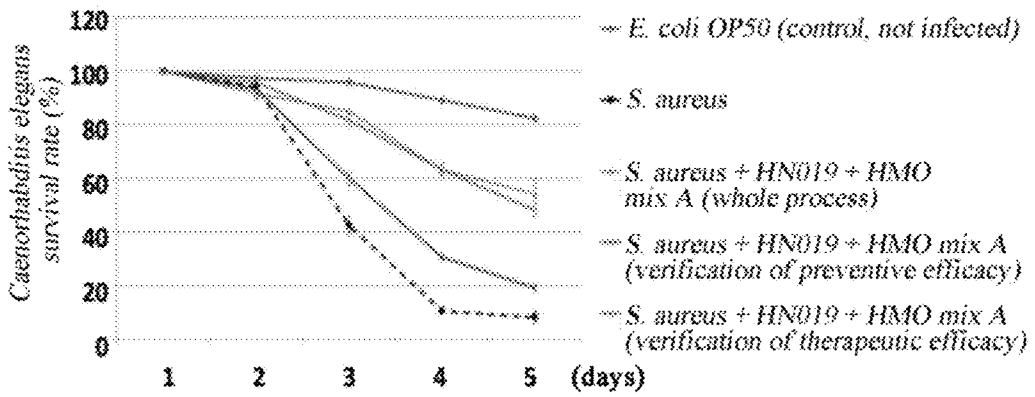
FIG. 7 shows the different effects of the co-culture of HN019 ($1\times10^8$ CFU) and HMO mix A (10 mg/mL) in improving the survival rate of *C. elegans* before and/or during *S. aureus* infection.

The results are shown in FIG. 7. The survival curve shows that from Day 1 to Day 5 after culturing, no matter whether the test substances were added to the co-culture before the infection or during the infection, there was an improvement in the survival rate and protection for nematodes under an infecting condition with *Staphylococcus aureus*. Both the case where the test substances were added to the nematodes during *Staphylococcus aureus* infection, and the case where the test substances were present in the whole process, had similar effects in terms of the improvement in survival rate and protection against *Staphylococcus aureus*. Furthermore, as compared with the case where the test substances were added only before the infection, stronger protection for the survival of nematodes was seen in both the case where the test substances were added during the infection and the case where the test substances were present in the whole process.

Figure 8:
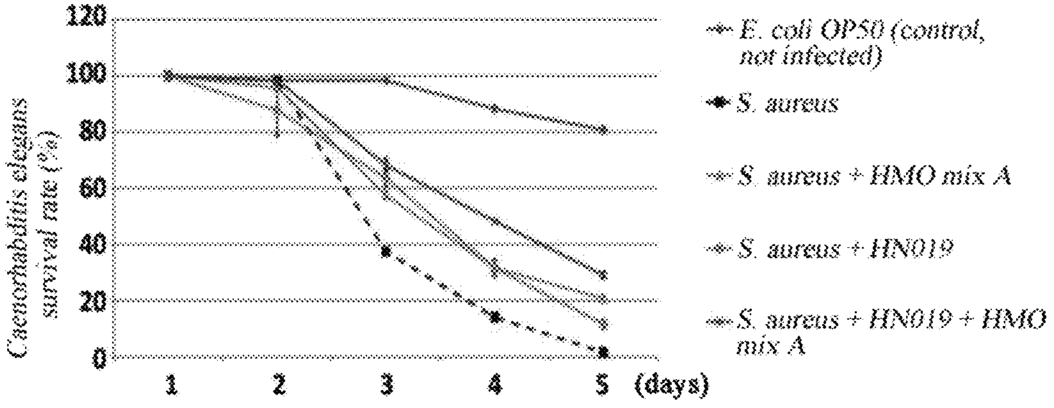
FIG. 8 shows the effects of HMO mix A (8 mg/mL) and *Bifidobacterium lactis* HN019 ($1\times10^8$ CFU), alone and in combination, on the survival rate of *C. elegans* infected by *Staphylococcus aureus*.

2. Effect of HMO Mix a (8 mg/mL) and *Bifidobacterium lactis* HN019, Alone or in Combination, on the Survival Rate of Nematodes Under *Staphylococcus aureus* Infection The results are shown in FIG. 8. It can be seen that from Day 1 to Day 5 after culturing, both the HMO mix A alone at 8 mg/mL and the probiotic HN019 ($10^8$ cfu) alone can significantly improve the survival rate of nematodes under an infecting condition with *Staphylococcus aureus*, and when they were combined, the improvement was even more significant ($P<0.0001$). This suggests there is an excellent synergistic effect between the probiotic HN019 and HMO mix A (8 mg/mL).

Figure 9:
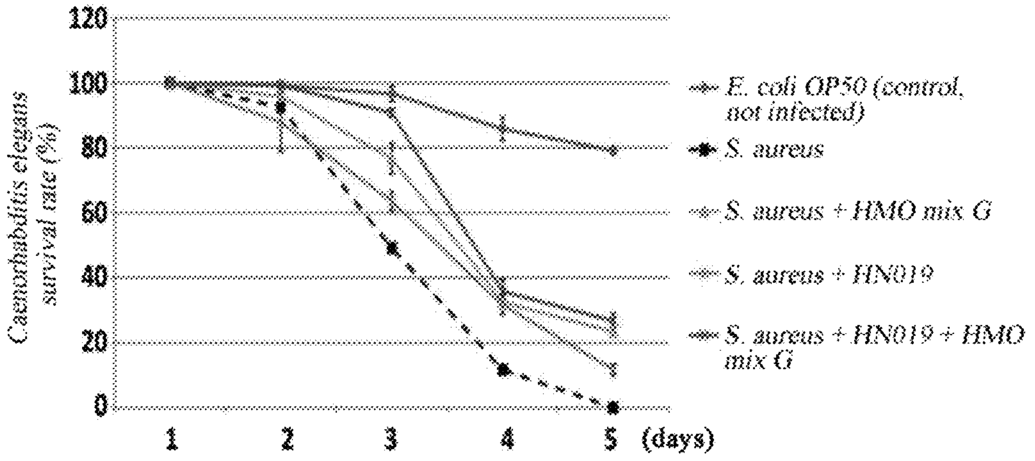
FIG. 9 shows the effects of HMO mix G (8 mg/mL) and *Bifidobacterium lactis* HN019 ($1\times10^8$ CFU), alone and in combination, on the survival rate of *C. elegans* infected by *Staphylococcus aureus*.

3. Effect of HMO Mix G (8 mg/mL) and *Bifidobacterium lactis* HN019, Alone or in Combination, on the Survival Rate of Nematodes Under *Staphylococcus aureus* Infection The results are shown in FIG. 9. It can be seen that from Day 1 to Day 5 after culturing, both HMO mix G alone at 8 mg/mL and the probiotic HN019 ($10^8$ cfu) alone can significantly improve the survival rate of nematodes under an infecting condition with *Staphylococcus aureus*, and when they were combined, the improvement was even more significant. This suggests there is an excellent combinational effect between the probiotic HN019 and HMO mix G (8 mg/mL).

Figure 10:
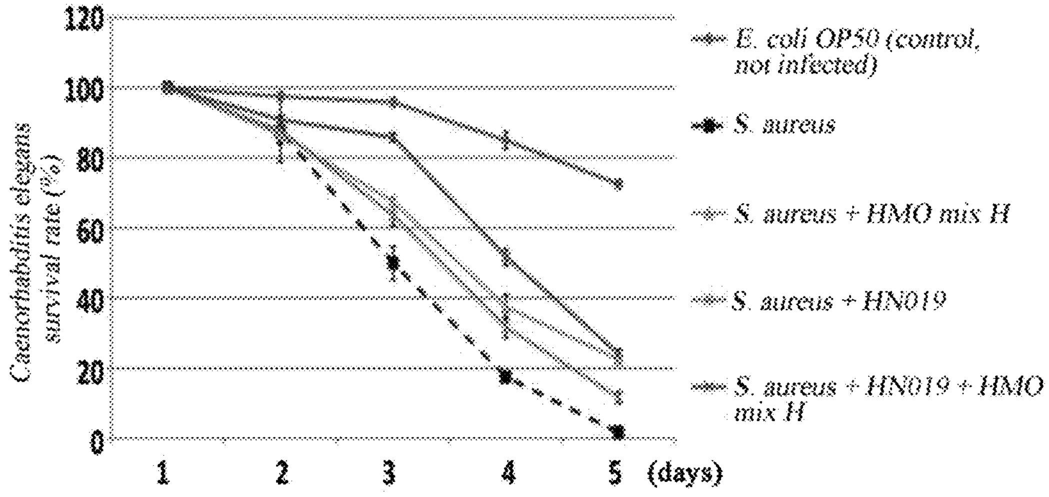
FIG. 10 shows the effects of HMO mix H (8 mg/mL) and *Bifidobacterium lactis* HN019 ($1\times10^8$ CFU), alone and in combination, on the survival rate of *C. elegans* infected by *Staphylococcus aureus*.

4. Effect of HMO Mix H (8 mg/mL) and *Bifidobacterium lactis* HN019, Alone or in Combination, on the Survival Rate of Nematodes Under *Staphylococcus aureus* Infection The results are shown in FIG. 10. It can be seen that from Day 1 to Day 5 after culturing, both HMO mix H alone at 8 mg/mL and the probiotic HN019 ($10^8$ cfu) alone can significantly improve the survival rate of nematodes under an infecting condition with *Staphylococcus aureus*, and when they were combined, the improvement was even more significant. This suggests there is an excellent combinational effect between the probiotic HN019 and HMO mix H (8 mg/mL).

Example 3: Infant Formula Powder with Addition of a Composition of a HMO Mix and *Bifidobacterium lactis* HN019

This example provided formula powder for infant 0-6 months old. In this formula powder, the total protein content was 11.1 g/100 g powder, the fat content was 28.3 g/100 g powder, the carbohydrate content was 52.9 g/100 g powder, the content of the HMO mix was 2.5 g/100 g powder, and the *Bifidobacterium lactis* was $4\times10^8$ CFU/100 g. The components and their ratio in the HMO mix were: 2'-fucosyllactose (2'-FL):3'-fucosyllactose (3'-FL):lactose-N-tetraose (LNT):3'-sialyllactose (3'-SL):6'-sialyllactose (6'-SL)=53:21:16:5:5.

What is claimed is:

1. A composition for enhancing resistance of an organism to *Staphylococcus aureus* infection, improving innate immunity of an organism, and/or anti-aging, consisting of *Bifidobacterium lactis* and human milk oligosaccharides (HMOs);

wherein the *Bifidobacterium lactis* is the strain *Bifidobacterium lactis* HN019;

wherein the HMOs consist of 2'-fucosyllactose, 3'-fucosyllactose, lactose-N-tetraose, 3'-sialyllactose, and 6'-sialyllactose in a weight ratio of (5% to 53%):(21% to 41%):(16% to 32%):(5% to 22%):(0% to 5%).

2. The composition according to claim 1, wherein the ratio of the *Bifidobacterium lactis* to the HMOs is ($1\times10^3$ to $1\times10^{12}$ CFU):(0.1 gram to 10 g).

3. The composition according to claim 2, wherein the ratio of the *Bifidobacterium lactis* to the HMOs is ($1\times10^6$ to $1\times10^{10}$ CFU):(1 g to 10 g).

4. A food product comprising the composition according to claim 1;

the *Bifidobacterium lactis* in the food product is used in an amount of $1\times10^3$ to $1\times10^{12}$ CFU per day.

5. The food according to claim 4, wherein the HMOs include at least three or four of 2'-fucosyllactose, 3'-fucosyllactose, lactose-N-tetraose, 3'-sialyllactose, and 6'-sialyllactose in a weight ratio of (0% to 73%):(0% to 61%):(0% to 52%):(0% to 42%):(0% to 25%); or the HMOs include 2'-fucosyllactose, 3'-fucosyllactose, lactose-N-tetraose, 3'-sialyllactose, and 6'-sialyllactose in a weight ratio of (0% to 53%):(21% to 41%):(16% to 32%):(5% to 22%):(0% to 5%).

6. The food product according to claim 4, wherein the HMOs in the food product are used in a total amount of 0.015 g to 15 g per day.

7. The food product according to claim 4, wherein the HMOs in the food product are used in a total amount of 0.1 g to 12 g per day.

8. The food product according to claim 4, wherein the HMOs in the food product are used in a total amount of 1.5 g to 10 g per day.

9. A method for enhancing resistance of an organism to *Staphylococcus aureus* infection, improving innate immunity of an organism, and/or anti-aging, comprising:

administering to the organism an effective amount of a composition consisting of *Bifidobacterium lactis* and human milk oligosaccharides (HMOs);

wherein the *Bifidobacterium lactis* is the strain *Bifidobacterium lactis* HN019;

wherein the HMOs consist of 2'-fucosyllactose, 3'-fucosyllactose, lactose-N-tetraose, 3'-sialyllactose, and 6'-sialyllactose in a weight ratio of (5% to 53%):(21% to 41%):(16% to 32%):(5% to 22%):(0% to 5%).

10. The method according to claim 9, wherein the enhancing resistance of an organism to *Staphylococcus aureus* infection includes:

enhancing an individual's ability to prevent *Staphylococcus aureus* infection, reducing the ability of *Staphylococcus aureus* to infect an individual, and/or alleviating food poisoning, enteritis, pneumonia, skin infection, wound ulceration, and/or meningitis caused by *Staphylococcus aureus* infection in an individual.

11. The method according to claim 9, wherein the composition is administered to the organism in the form of a food product, wherein the food product is a liquid beverage, a solid beverage, an oral liquid, a diary product, a tablet, or a capsule;

the *Bifidobacterium lactis* in the food product is used in an amount of $1\times10^3$ to $1\times10^{12}$ Colony-Forming Units (CFU);

the HMOs in the food product are used in a total amount of 0.015 g to 15 g per day.

12. The method according to claim 11, wherein the *Bifidobacterium lactis* in the food product is used in an amount of $1\times10^6$ to $1\times10^{11}$ CFU per day;

the HMOs in the food product are used in a total amount of 0.1 g to 12 g per day.

13. The method according to claim 12, wherein the HMOs in the food product are used in a total amount of 1.5 g to 10 g per day.

14. The method according to claim 9, wherein the HMOs include 2'-fucosyllactose, 3'-fucosyllactose, lactose-N-tetraose, 3'-sialyllactose, and 6'-sialyllactose in a weight ratio of 53%:21%:16%:5%:5%.

* * * * *